United States Patent
Harang

(10) Patent No.: US 6,235,719 B1
(45) Date of Patent: May 22, 2001

(54) USES OF COMPOSITIONS WITH α-LACTALBUMIN BASE

(75) Inventor: Benoît Harang, Sèvres (FR)

(73) Assignee: Laboratoire Oenobol, S.A., Paris (FR)

( * ) Notice: Subject to any disclaimer, the term of this patent is extended or adjusted under 35 U.S.C. 154(b) by 0 days.

(21) Appl. No.: 09/269,878

(22) PCT Filed: Oct. 3, 1997

(86) PCT No.: PCT/FR97/01752

§ 371 Date: Apr. 2, 1999

§ 102(e) Date: Apr. 2, 1999

(87) PCT Pub. No.: WO98/14204

PCT Pub. Date: Apr. 9, 1998

(30) Foreign Application Priority Data

Oct. 3, 1996 (FR) .................................................. 96/12064

(51) Int. Cl.⁷ .......................... A61K 38/00; A61K 31/70; A61K 31/045
(52) U.S. Cl. ................. 514/23; 514/21; 514/724
(58) Field of Search ................. 514/23, 21, 724

(56) References Cited

U.S. PATENT DOCUMENTS

| | | | |
|---|---|---|---|
| 4,485,040 | 11/1984 | Roger et al. | 260/122 |
| 4,639,465 | 1/1987 | Pollack et al. | 514/419 |
| 4,650,789 | 3/1987 | Pollack | 514/23 |

FOREIGN PATENT DOCUMENTS

WO 91/10441  7/1991 (WO).

OTHER PUBLICATIONS

W. Heine et al., The Significance of Tryptophan in Human Nutrition, *Amino Acids,* 9(3):191–205 (1995).

G. Hajak et al., The Influence of Intravenous L–tryptophan on Plasma Melatonin and Sleep in Men , *Pharmacopsychiatry,* 24:17–20 (1991).

*Primary Examiner*—Theodore J. Criares
(74) *Attorney, Agent, or Firm*—Morgan, Lewis & Bockius LLP

(57) ABSTRACT

The invention concerns novel uses of α-lactalbumen and compositions containing it, as nutritional complement and as medicine, for regulating sleep and the biological clock controlling the sleeping/waking cycle.

8 Claims, No Drawings

USES OF COMPOSITIONS WITH α-LACTALBUMIN BASE

This application is a 371 of PCT/FR97/01752 filed Oct. 3, 1997 which claims priority of French Application 96/12064 filed Oct. 3, 1996.

The present invention relates to new uses of α-lactalbumen as well as to compositions containing it, as a nutritional supplement and as a medicament, in the regulation of sleep and of the biological clock controlling the wake/sleep cycle.

The circadian rhythm which controls the activity of plants and animals determines when and how to sleep. Lasting from 2 minutes to 25 minutes, this cycle covers the 24 hours which make up a day. Dozens of internal clocks are responsible for synchronizing living organisms both internally and in relation to the environment. These internal rhythms control and coordinate hormone production, hunger, mood, the temperature of the body and the energy level. An internal clock also controls the wake/sleep cycle.

The pineal gland (epiphysis) and the hypothalamus jointly control the wake/sleep cycles. Under the effect of darkness, the epiphysis releases melatonin. The melatonin level reaches its maximum between 1 and 5 am. Then at dawn, light inhibits the secretion of melatonin. Light penetrates into the brain along the route which goes from the retina to the epiphysis via the suprachiasmatic nucleus, in the hypothalamus. The epiphysis then slows down the production of melatonin. This ability of the pineal gland is therefore essential for maintaining our circadian rhythms.

To synthesize melatonin, the epiphysis needs precursors. Tryptophan (Trp), an essential amino acid, is the natural precursor of melatonin after a first step of conversion to serotonin. It is therefore necessary that the tryptophan pool is sufficient at the time when the epiphysis increases its activity, that is to say during sleep.

Melatonin is derived from serotonin, a neuromediator produced by the neurons from tryptophan which the body is incapable of synthesizing (essential amino acid) and which must be provided by the diet. However, the use of this amino acid in the neurons poses a delicate problem of biological interactions.

Trp, after digestion of protein containing it, is transported by the blood up to the brain. This passage of the blood-brain barrier is an active transport and the Trp is in competition with 5 other amino acids: valine, leucine, tyrosine, isoleucine and phenylalanine. The ingestion of proteins favors the 5 neutral amino acids because they exist in a high proportion in proteins whereas Trp is the most rare amino acid in proteins.

Once brought to the neuron, tryptophan is hydroxylated to 5-hydroxytryptophan, which is itself decarboxylated to 5-hydroxytryptamine (serotonin). Serotonin will then undergo, in the epiphysis, an N-acetylation and then a 5-methylation, which lead to the formation of N-acetyl-5-methoxytryptamine, melatonin.

Hydroxyindole-O-methyltransferase (HIOMT), an enzyme catalyzing the final step in the synthesis of melatonin, is found in particular in the pineal gland. Its activity is reduced by light and this effect is prevented by sympathectomy.

Serotonin can be catabolized by amine oxidases and excreted in the urine in the form of 5-hydroxyindole-3-acetic acid.

Melatonin is highly lipophilic and diffuses from the epiphysis into the blood stream, rapidly reaching the other biological fluids such as saliva and the cerebrospinal, seminal, ovarian, follicular and amniotic fluids. It is recognized that the plasma melatonin concentration is a good marker of the physiological activity of the epiphysis. Melatonin is metabolized in the liver to its hydroxylated derivative, which is mainly conjugated with sulfuric acid: 6-hydroxymelatonin sulfate (oral absorption of melatonin leads to the hepatic first pass effect). About 1% of melatonin is excreted in the urine in its native form; the majority is eliminated in the form of its metabolite 6-hydroxymelatonin sulfate.

A study published in 1991 has shown that the intravenous administration of tryptophan increases the secretion of melatonin (G. HAJAK et al., Pharmacopsychotherapy, 1991, 24, 17–20, The influence of intravenous L-tryptophan on plasma melatonin and sleep in men).

Moreover, numerous studies have related to the importance of Trp depletion in mood and wake/sleep balance disruptions, as well as, conversely, on the influence of protein diet and of amino acids on cerebral function.

Finally, a recent review has shown the importance of milk proteins and particularly of α-lactalbumin as a nutritional source of tryptophan (W. HEINE et al., Amino Acids, 1995, 9, 191–205, The significance of tryptophan in human nutrition).

The Applicant has now found, unexpectedly, that the ingestion, by the oral route, of a composition based on α-lactalbumin, with no supply of sugar and not combined with other amino acids, and despite the competition with neutral amino acids, does not prevent the absorption of tryptophan at the level of the blood-brain barrier and plays the role of melatonin precursor, with, as a corollary, a significant increase in the melatonin level secreted during the night; this allows the use of such a composition as a sleep and biological clock regulator. This justifies in particular the importance of a nutritional supplementation with tryptophan-rich proteins a few tens of minutes before falling asleep.

The subject of the present invention is the use of a composition essentially consisting of α-lactalbumin, at a unit dose of between 100 mg and 250 mg, for the preparation of a nutritional supplement which is to be used by the oral route, in the regulation of sleep and/or the biological clock controlling the wake/sleep cycle.

Unexpectedly, the use, by the oral route, of such a composition comprising only α-lactalbumin as protein makes it possible to obtain a daily tryptophan supply of about 30–70 mg which is effectively capable of regulating sleep and the biological clock controlling the wake/sleep cycle.

The subject of the present invention is also the use of a composition essentially consisting of α-lactalbumin, at a unit dose of between 375 mg and 1 g, for the preparation of a medicament intended to be used in the treatment, by the oral route, of sleep disorders and/or of disorders of the biological clock controlling the wake/sleep cycle in humans.

The subject of the present invention is also a nutritional supplement capable of regulating sleep and/or the biological clock controlling the wake/sleep cycle, characterized in that it essentially consists of α-lactalbumin at a unit dose of between 100 mg and 250 mg and of at least one technological adjuvant.

Unit dose is understood to mean the quantity of α-lactalbumin present in an administerable unit of nutritional supplement.

For example, such a nutritional supplement, which comprises 100 to 250 mg of α-lactalbumin per administerable unit, is administered by the oral route, at a daily dosage of 2 to 4 units, in order to obtain the desired daily quantity (400 mg to 1 g).

The subject of the present invention is also a medicament intended for the treatment of disorders of the biological clock controlling the wake/sleep cycle and/or of sleep disorders, characterized in that it essentially consists of α-lactalbumin at a unit dose of between 375 mg and 1 g and of at least one technological adjuvant.

Such a medicament, which comprises 375 mg to 1 g of α-lactalbumin per administerable unit, is administered by the oral route, at a daily dosage of 2 to 4 units in order to obtain the desired daily quantity (1.5 g to 4 g).

According to an advantageous embodiment of said nutritional supplement or of said medicament, the α-lactalbumin is present in lyophilized form.

Said technological adjuvant is appropriate for the formulation chosen: capsule, tablet, sachet or oral solution and is in particular selected from lubricants, such as magnesium stearate, products for instant solubilization in aqueous solution, gelling agents or any other adjuvant.

In addition to the preceding arrangements, the invention also comprises other arrangements which will emerge from the description which follows, which refers to exemplary embodiments of the method which is the subject of the present invention.

It should be clearly understood, however, that these examples are given solely by way of illustration of the subject of the invention and do not constitute in any manner a limitation thereto.

EXAMPLE 1

Composition According to the Invention

The α-lactalbumin used is either in purified form, or in the form of a protein fraction from cow's milk, in which the α-lactalbumin content is of the order of 50%; gelatin capsules prepared from such a protein fraction have in particular the following composition:

|  | per gelatin capsule | per day 2 gelatin capsules | 4 gelatin capsules |
|---|---|---|---|
| Milk protein fraction in lyophilized powder form | 225 mg | 450 mg | 900 mg |
| Gelatin | 112.8 mg | | |
| Lactose | 7.52 mg | | |
| Magnesium stearate | 6.7 mg | | |

More specifically, this protein fraction exhibits the following amino acid distribution:

| Average amino acid composition (g/100 g of protein) | | | |
|---|---|---|---|
| Aspartic acid | 14.8 | Isoleucine | 5.7 |
| Threonine | 8.7 | Leucine | 10.4 |
| Serine | 7.6 | Tyrosine | 4.3 |
| Glutamic acid | 17.3 | Phenylalanine | 4.8 |
| Proline | 5.6 | Lysine | 7.8 |
| Glycine | 3.1 | Histidine | 2.6 |
| Alanine | 4.0 | Arginine | 3.6 |
| Valine | 6.8 | Cysteine | 4.4 |
| Methionine | 2.0 | Tryptophan | 3.0 |

EXAMPLE 2

Role of the Melatonin Precursor of a Composition According to Example 1

Protocol:

Five subjects are necessary for the evaluation of "the promelatonin activity" of a composition according to Example 1.

This activity is determined by assaying the urinary metabolite of melatonin in the first morning urine.

It is an open randomized monocenter study including five subjects. The effects of the absorption of 2 doses of α-lactalbumin with or without carbohydrate supplementation are analyzed.

The duration of the study is 10 days.

The study is carried out according to the protocol illustrated in Table I below:

| Selection | | |
|---|---|---|
| | Evaluation without supplementation | Evaluation with supplementation |
| V<br>V = visits<br>Description | D1 D2 D3 D4 | D5 D6 D7 D8 D9 D10 |
| Days | D1 D2 D3 D4 | D5 D6 D7 DB D9 D10 |
| Visit | V1 | V2 |
| clinical examination | * | * |
| supplementation | | according to Latin square (Table II), randomization No. 0, 1, 2, 3, 4 |
| collection of urine | | |
| | * * * * | * * * * * * |
| Drafting of the questionnaire | | * |
| Informed consent | * | |
| Undesirable effects | | * * * * * * * * |

Each subject receives a packet of 10 sachets containing 0 geLatin capsules for two of them, 2 geLatin capsules for 4 of them and 4 geLatin capsules for the other four in order to provide a daily dose of: 0 geLatin capsules (0), 2 geLatin capsules (1 and 2) or 4 geLatin capsules (3 and 4).

The gelatin capsules are taken with a glass of moderately warm milk which is unsweetened for 1 and 3, or sweetened (the equivalent of one No. 4 lump) for 2 and 4, about 1 hour before the expected time of going to bed.

Results:

The efficacy of this treatment is determined by an increase in the urinary excretion of 6-hydroxymelatonin sulfate (6-SMT) after the various supplementation conditions (dosage, concomitant ingestion of sugar) described in Table II or in the absence of supplementation, the subject being his own control. The treatments were distributed according to the Latin square method.

TABLE II

Randomization model for the study

| | D1 | D2 | D3 | D4 | D5 | D6 | D7 | D8 | D9 | D10 |
|---|---|---|---|---|---|---|---|---|---|---|
| S1 | 0 | 0 | 1 | 1 | 2 | 2 | 3 | 3 | 4 | 4 |
| S2 | 1 | 1 | 2 | 2 | 3 | 3 | 4 | 4 | 0 | 0 |
| S3 | 2 | 2 | 3 | 3 | 4 | 4 | 0 | 0 | 1 | 1 |

TABLE II-continued

Randomization model for the study

|    | D1 | D2 | D3 | D4 | D5 | D6 | D7 | D8 | D9 | D10 |
|----|----|----|----|----|----|----|----|----|----|-----|
| S4 | 3  | 3  | 4  | 4  | 0  | 0  | 1  | 1  | 2  | 2   |
| S5 | 4  | 4  | 0  | 0  | 1  | 1  | 2  | 2  | 3  | 3   |

S1 = subject 1, S2 = subject 2, S3 = subject 3, S4 = subject 4; 0 = no supplementation, 1 = 2 capsules/day without sugar, 2 = 4 capsules/day without sugar, 3 = 2 capsules/day with sugar, 4 = 4 capsules/day with sugar.

The biological parameters are analyzed with the aid of the Student statistical test according to the ANOVA method (factorial analysis).

The mean quantities of 6-SMT excreted in the urine and determined by RIA, relative to the urinary creatinine concentration, are illustrated in Table III.

TABLE III assay of 6-SMT (ng) per mg of creatinine (mean of two assays) and results of comparison by ANOVA between the four treatments

| Subject | α-lactalbumin supplementation | | | | | ANOVA | |
|---------|------|-------|---------|---------|-------|------|------|
|         | 0    | 1     | 2       | 3       | 4     | F    | P    |
| S1      | 25.7 | 24.9  | 32.6    | 20.1    | 25.5  | 1.12 | 0.44 |
| S2      | 13.7 | 17.5  | 17.7    | $19.2^1$| 15.1  | 1.50 | 0.33 |
| S3      | 37.5 | 37.1  | $39.4^2$| 21.5    | 39.5  | 1.79 | 0.27 |
| S4      | 41.4 | 30    | $32.4^3$| 22.3    | $37.5^4$ | 0.55 | 0.70 |
| S5      | 7.34 | 9.85  | $14.9^5$| 10.5    | 11.5  | 2.80 | 0.14 |

1: significant versus 0 (90%); 2: significant versus 3 (90%); 3: significant versus 3 (90%); 4: significant versus 3 (90%); 5: significant versus 0 (95%); versus 1 (90%).

The measurements, which are analyzed with the aid of a Student statistical test according to the ANOVA method (analysis repeated), show that the secretion of melatonin is not influenced by the time of supplementation for each subject (F[probability factor (Student's table)]=0.64, df [degree of freedom]=4, p [probability]=0.81).

The analysis according to the Student's test according to the ANOVA method (factorial analysis) reveals a significant increase in melatonin secretion for 3 subjects (S1, S3 and S5) after 4 capsules/d and 1 subject after 2 capsules/d.

A dose of carbohydrate has no significant effect on the urine secretion of 6-SMT.

For one of the subjects (S4), no significant difference was observed after supplementation and is due to the problem which emerged that this subject was drinking a glass of alcohol before going to bed.

The results obtained suggest that the oral administration of α-lactalbumin (corresponding to 30–70 mg/d of tryptophan) significantly increases the urine excretion of 6-SMT.

Surprisingly, the oral administration of tryptophan, in the form of α-lactalbumin, at a concentration greater than 30–70 mg/d, significantly increases the secretion of melatonin in healthy subjects.

As is evident from the above, the invention is not at all limited to its embodiments, implementations and applications which have just been described more explicitly; it encompasses on the contrary all the variants which may occur to the specialist in this field, without departing from the framework or the scope of the present invention.

What is claimed is:

1. A method to regulate sleep or the biological clock controlling the wake/sleep cycle, comprising the administration of an effective amount of α-lactalbumin that is not combined with free amino acids and peptides rich in arginine or ornithine.

2. The method of claim 1, wherein the α-lactalbumin is administered at a unit dose of about 100 mg to about 250 mg.

3. A method to treat sleep disorders or disorders of the biological clock controlling the wake/sleep cycle, comprising the administration of an effective amount of α-lactalbumin that is not combined with free amino acids and peptides rich in arginine or ornithine.

4. The method of claim 3, wherein the α-lactalbumin is administered at a unit dose of about 375 mg to about 1 g.

5. A method to regulate sleep or the biological clock controlling the wake/sleep cycle, comprising the administration of an effective amount of a composition consisting essentially of α-lactalbumin.

6. The method of claim 5, wherein the α-lactalbumin is lyophilized.

7. A method to treat sleep disorders or disorders of the biological clock controlling the wake/sleep cycle, comprising the administration of an effective amount of a composition consisting essentially of α-lactalbumin.

8. The method of claim 7, wherein the α-lactalbumin is lyophilized.

* * * * *